United States Patent [19]

Jasmine

[11] Patent Number: 4,734,609

[45] Date of Patent: Mar. 29, 1988

[54] GAS DENSITY TRANSDUCER

[75] Inventor: Richard Jasmine, Menlo Park, Calif.

[73] Assignee: Calogic Corporation, Fremont, Calif.

[21] Appl. No.: 890,661

[22] Filed: Jul. 25, 1986

[51] Int. Cl.$^4$ .................... H01L 41/08; G01N 31/00; G01L 11/00

[52] U.S. Cl. ....:.................... 310/315; 73/30; 73/703; 73/708; 310/311; 310/312; 310/338; 310/370; 310/317; 310/319

[58] Field of Search ............... 310/311, 312, 338, 315, 310/342, 344, 319, 317, 370; 73/29, 30, 26, 27, 28, DIG. 4, 702, 703, 708, 861.42, 861.44, 861.45

[56] References Cited

U.S. PATENT DOCUMENTS

| | | | |
|---|---|---|---|
| 3,045,491 | 7/1962 | Hart | 310/338 X |
| 3,844,174 | 10/1974 | Chabre | 310/312 |
| 3,879,992 | 4/1975 | Bartera | 310/311 X |
| 3,902,355 | 9/1975 | Weisser | 73/702 X |
| 4,223,524 | 9/1980 | Nakagawa | 310/315 X |
| 4,227,182 | 10/1980 | Ogasawara et al. | 73/DIG. 4 |
| 4,456,892 | 6/1984 | Vandergraaf | 310/315 X |
| 4,479,070 | 10/1984 | Frische et al. | 310/338 |
| 4,507,970 | 4/1985 | Dinger | 310/370 X |
| 4,558,248 | 12/1985 | Valentin | 310/315 |

*Primary Examiner*—Mark O. Budd
*Attorney, Agent, or Firm*—Townsend and Townsend

[57] ABSTRACT

An improved gas density transducer which compares the resonant frequency of an enclosed, reference tuning fork crystal oscillator with the resonant frequency of a detector tuning fork crystal oscillator exposed to the surrounding gas. The frequency of oscillation of the detector crystal oscillator exposed will vary in accordance with the gas density because of the motional resistance of the gas to vibrations of the tuning fork oscillator. The frequency of the detector oscillator can be compared to the frequency of the reference oscillator to determine the gas density.

16 Claims, 5 Drawing Figures

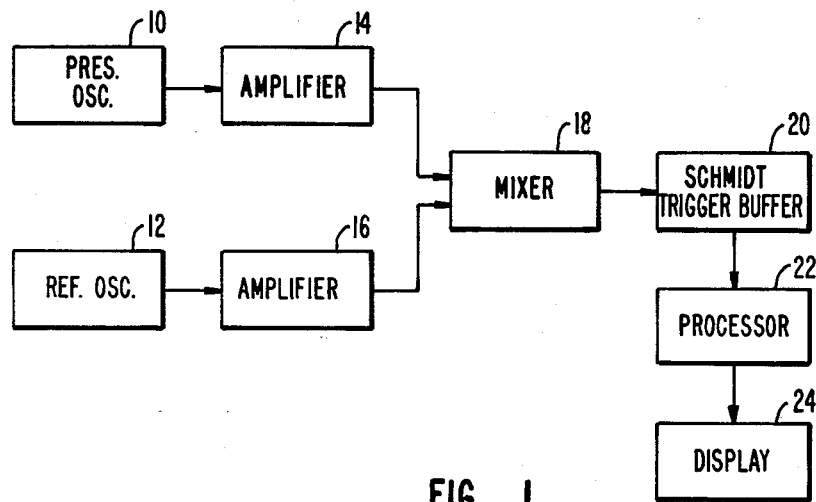
FIG._1.
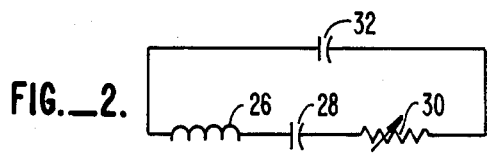
FIG._2.
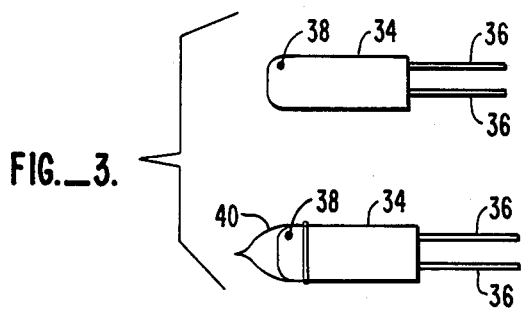
FIG._3.

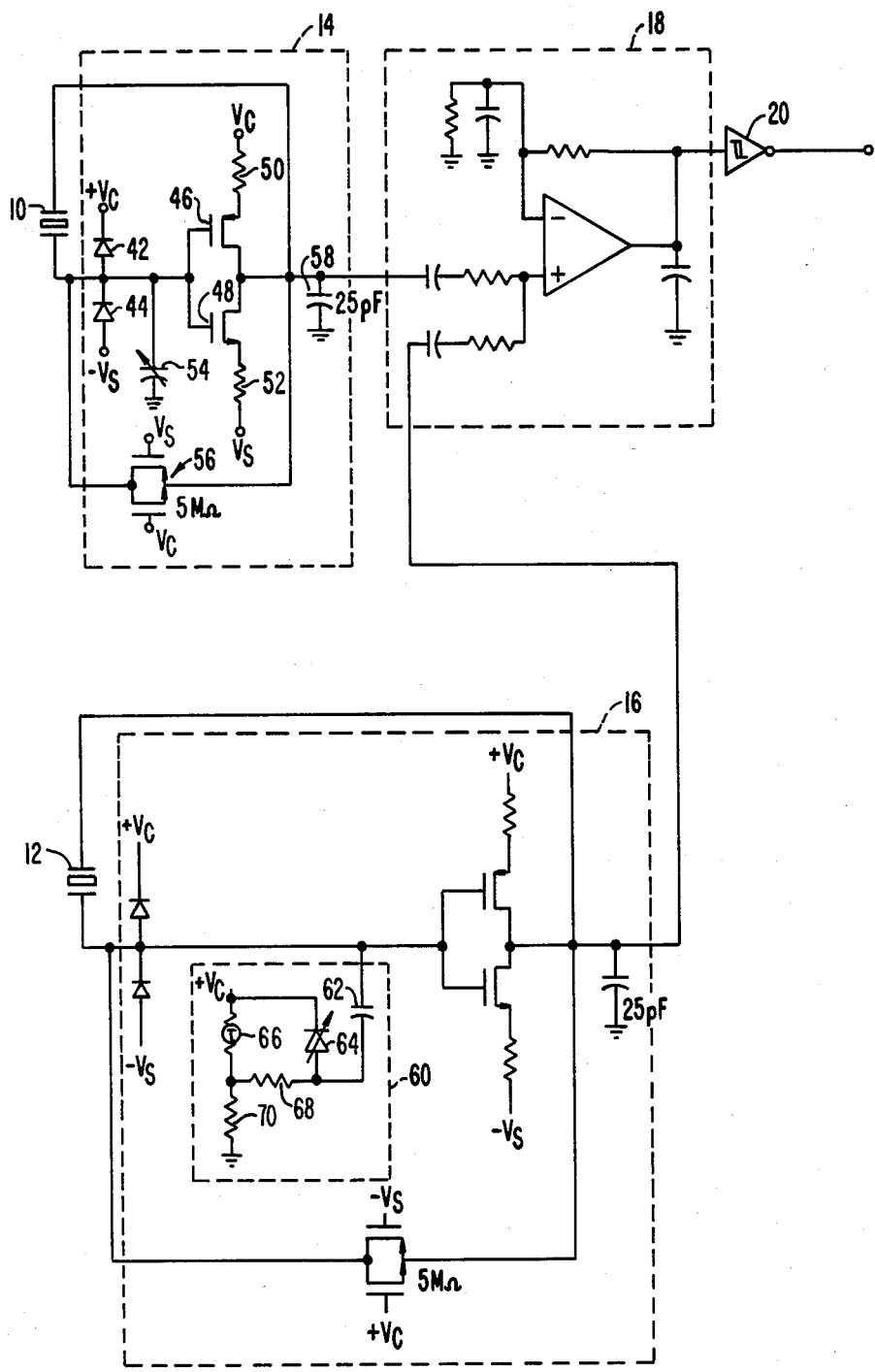
FIG._4.

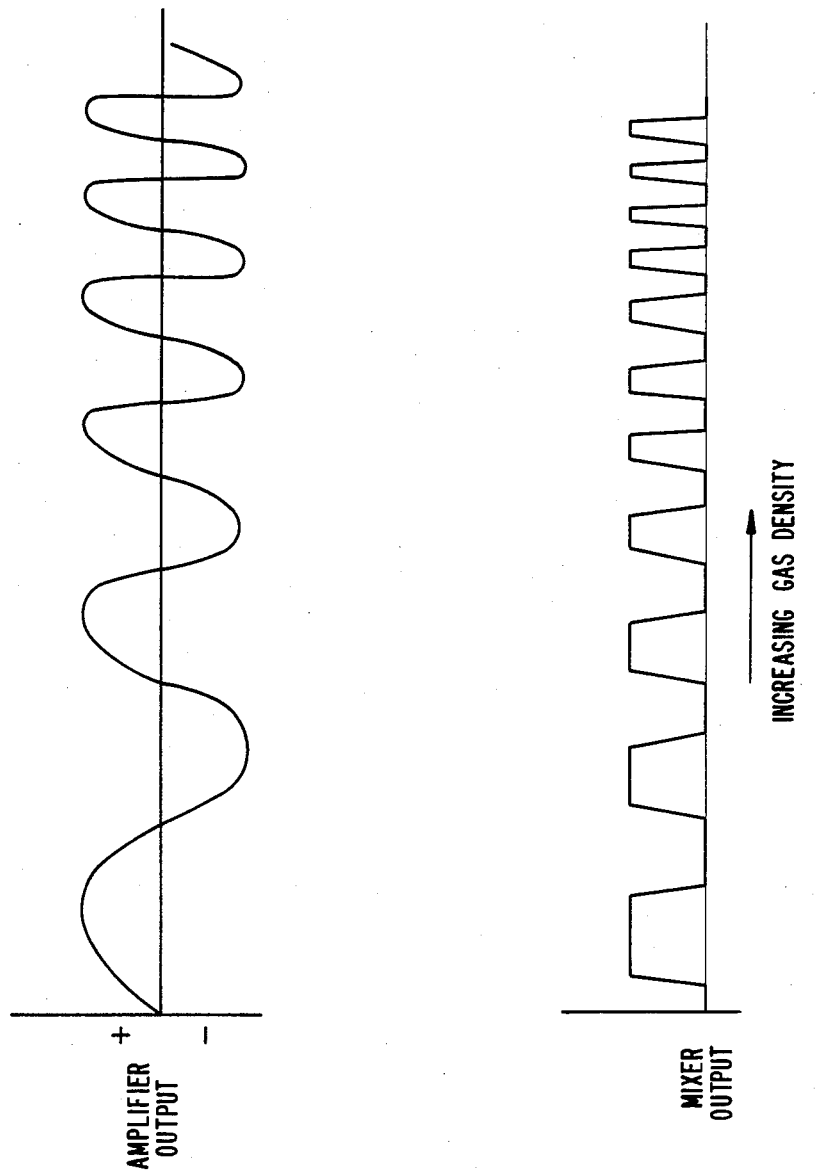

GAS DENSITY TRANSDUCER

BACKGROUND

The present invention relates to instruments for measuring gas density or pressure and more particularly to consumer pressure gauges, altimeters and the like.

Many different methods and devices exist for measuring gas pressure and density. Many use complex mechanical arrangements. For example, in U.S. Pat. No. 3,745,384 to Blanchard, a diaphram which has a varying resonant frequency depending upon the pressure applied is used with a feedback circuit for maintaining resonance.

Piezoelectric materials are used in a number of gauges. Pressure is applied to one side of the piezoelectric material, often a quartz crystal, causing stress in the piezoelectric material and thereby changing its electrical characteristics, which change can be measured by a variety of methods. See, for instance, U.S. Pat. No. 2,558,563 to Janssen, U.S. Pat. No. 3,479,536 to Norris, U.S. Pat. No. 3,903,733 to Murayama, et al. and U.S. Pat. No. 4,175,423 to Braun, et al. These devices use different mechanical mounting methods which can be quite complex.

Piezoelectric materials, such as quartz crystals, can also be caused to oscillate by the application of an external voltage. Pressure can be applied to deform the crystal and change the frequency of oscillation. The changed frequency of oscillation can be measured to determine variations in gas density or pressure. A difficulty with this method is the damping effect on oscillations if pressure is directly applied, and the hysteresis effects if pressure is applied to the edges of the crystal. Complex mechanical provisions to transmit force to the crystal without causing damping or hysteresis effects have been developed. See, for instance, U.S. Pat. No. 3,561,832 to Karrer, et al., U.S. Pat. No. 4,562,375 to Besson, et al. and U.S. Pat. No. 4,550,610 to EerNisse.

An alternate method shown in U.S. Pat. No. 3,879,992 to Bartera, uses a device which has at least two crystals, each of which is coated with a different type of gas absorbing coating. The different coatings will absorb different types of gases (such as $H_2O$ or $CO_2$). The increased mass of the crystal will vary its frequency of oscillation, with the amount of mass absorbed being proportional to the frequency of oscillation, thereby enabling the detection of a particular type of gas by monitoring the change in frequency. All of the crystals used are exposed to the same air environment with different gases being detected by the different sensitivities of the coatings on the crystals.

There is a need for a gas density transducer which is simple and economical for use in consumer items. Many of the discussed prior art devices are expensive and complex, requiring expensive electronic support equipment and thus warranting use only in complex systems such as military aircraft, oil well monitoring equipment or the like where cost is less critical, and being unpractical for consumer applications, such as portable battery powered applications in altimeters for bicycles, watches, cars, etc.

SUMMARY OF THE INVENTION

The present invention is an improved gas density transducer which compares the resonant frequency of an enclosed, reference tuning fork crystal oscillator with the resonant frequency of a detector tuning fork crystal oscillator exposed to the surrounding gas. The frequency of oscillation of the detector crystal oscillator exposed will vary in accordance with the gas density because of the motional resistance of the gas to vibrations of the tuning fork oscillator. The frequency of the detector oscillator can be compared to the frequency of the reference oscillator to determine the gas density. For most consumer applications, the gas is air.

Preferably, two nearly identical tuning fork type crystal oscillators in hermetically sealed packages are used. The reference oscillator is sealed in its package in a vacuum, while a hole is produced in the detector oscillator package to expose it to the surrounding gas. The signals from the two oscillators are separately amplified and applied to a mixer circuit to produce a beat frequency corresponding to the difference in frequency of the two oscillators. The output of the mixer is applied to a Schmitt trigger buffer to produce a pulse train with a frequency corresponding to the beat frequency, and thus proportional to the gas density.

The detector oscillator package can have a diaphram covering the hole which exposes the crystal to the surrounding gas. The diaphram will protect the crystal from the effects of the surrounding gas or from dirt or dust particles or the like. The pressure is transmitted through the diaphram so that the crystal oscillator feels the effect of the external gas pressure as a change in gas density which affects the motional resistance of the crystal.

Because gas density varies with temperature, temperature effects are eliminated by including a circuit which will vary the frequency of the reference crystal oscillator to compensate for variations due to temperature induced gas density changes. This circuit uses a thermistor which exhibits the inverse of the density/temperature response of the gas.

The present invention provides a gas density transducer which can detect variations in altitude of as little as one foot. The transducer is also virtually insensitive to variations in temperature in the normal consumer product temperature range of 32° F. to 113° F. The use of two simple tuning fork crystal oscillators produces a simple design which can be economically produced. The present invention can be used in a large number of consumer applications where low cost and ease of manufacturing are required. Examples are altimeters, pressure gauges, density meters and gas identification or contamination instruments.

For a fuller understanding of the nature and advantages of the invention, reference should be made to the ensuing detailed description taken in conjunction with the accompanying drawings.

DETAILED DESCRIPTION OF THE DRAWINGS

FIG. 1 is a block diagram of a gas density transducer according to the present invention;

FIG. 2 is a schematic diagram of an equivalent circuit for a tuning fork quartz crystal;

FIG. 3 is a diagram of a quartz crystal oscillator without a diaphram and with a diaphram;

FIG. 4 is a detailed schematic diagram of the gas density transducer of FIG. 1; and FIG. 5 is a diagram of the various signal waveforms of the circuit of FIG. 4.

DETAILED DESCRIPTION OF THE PREFERRED EMBODIMENTS

FIG. 1 is a block diagram of a gas density transducer according to the present invention. A reference oscillator 12 is a tuning fork type quartz crystal in a hermetically sealed package. A similar density detector oscillator 10 is exposed to the surrounding gas. Oscillators 12 and 10 are coupled through amplifiers 14 and 16, respectively, to a mixer 18. Mixer 18 produces a beat frequency corresponding to the difference in frequency of oscillators 10 and 12 and applies this beat frequency to a Schmitt trigger buffer 20. Schmitt trigger buffer 20 provides an output with fast rise and fall times and a frequency proportional to the beat frequency. A processor 22 receives the square wave output and decodes it to produce the gas density. The gas density value is then processed through an appropriate formula to produce the parameter of interest (altitude, barometric pressure, water depth, etc.) on display 24.

FIG. 2 is a schematic diagram of the equivalent electrical circuit of a tuning fork quartz crystal. An inductor 26 is in series with a capacitance 28 and a resistance 30, all of which are shunted by a capacitance 32. The motional resistance of the gas to the motion of the tuning fork while oscillating is represented by resistor 30 being a variable resistance. Accordingly, the frequency of oscillation varies in a linear relationship to the motional resistance of the gas surrounding the tuning fork oscillator.

FIG. 3 shows a conventional tuning fork quartz crystal oscillator in a package 34 having a pair of leads 36. A gas exposure hole 38 is drilled into the package to expose the internal crystal to the surrounding gas. Alternately, hole 38 can be covered by a diaphram 40 to prevent dust or other contaminants from becoming lodged on the quartz crystal while at the same time exposing the quartz crystal to the pressure of the external gas.

The transducer circuit of FIG. 1 is shown in more detail in FIG. 4. Density detector oscillator 10 is coupled to an amplifier 14, which is a modified Pierce oscillator. Diodes 42 and 44 couple one side of crystal 10 to a positive voltage $V_c$ and a negative voltage $V_s$, respectively. These diodes serve as static protection devices. Oscillator 10 is coupled to a pair of field effect transistors (FETs) 46 and 48, respectively. FETs 46 and 48 amplify the signal from crystal 10 in both the positive and negative directions producing a sine wave at the output of amplifier 14 which has a waveform as shown in FIG. 5. A pair of 40 kilohm resistors 50 and 52 couple FETs 46 and 48, respectively, to $V_c$ and $V_s$, respectively. These resistors are used for current limiting. A variable capacitor 54 is used to tune crystal 10 to the desired operational frequency.

A typical standard operational frequency for crystal 10 is 32768 Hz ± 20 parts per million (± 1.3 Hz). Capacitor 54 is used to tune oscillator 10 to the same frequency as oscillator 12 to compensate for this variation of up to 1.3 Hz which can be expected between two oscillators in evacuated containers with the same capacitance. Both oscillators in evacuated containers are tuned to the same frequency so that the difference in frequencies when the density oscillator is exposed to the outside gas will be solely due to the motional resistance of the gas. If crystal 12 is in an evacuated chamber, crystal 10 will produce a frequency, at the air pressure and density of sea level, which is approximately 6 Hz lower than the frequency of crystal 12.

A pair of FETs 56 are used to form a feedback resistor and a 25 picofarad capacitor 58 is used to complete the 180° phase shift necessary to sustain oscillation. Crystal 10 is effectively inductive and thus completes the phase shift. Feedback resistor 56 (preferably 5 megohms) sets the bias point for the amplifier in the linear region. This resistance is large enough so that it does not appreciably effect the phase of the feedback network.

Amplifier 16 is identical to amplifier 14 except that a temperature sensitive capacitance circuit 60 is used in place of capacitor 54. The temperature sensitive circuit is used to compensate for changes in air density due to temperature in an altitude measuring device, such as an altimeter. If the actual gas density (rather than altitude as determined from a density measurement) is the parameter of interest, circuit 60 is eliminated and a variable capacitor similar to capacitor 54 is substituted. Circuit 60 includes a capacitor 62, a varactor diode 64, a thermistor 66, and resistors 68 and 70. The effect of circuit 60 is to produce an effect on the frequency of crystal 12 which is the same as the effect on the frequency of density detector oscillator 10 caused by changes in gas density due to temperature changes. The temperature characteristics of thermistor 66 are the inverse of the density/temperature characteristics of a gas. When thermistor 66 changes the voltage on varactor 64, the varactor will change its capacitance which in turn corrects the operational frequency of crystal 12. Varactor diode 64 thus tunes crystal 12 in a linear fashion. Varactor diode 64 has a capacitance which varies to tune the oscillator (preferably from 5 to 15 picofarads). Capacitor 62 is used as a DC isolation capacitor and resistance 68 has a value between one and 10 megohms.

The temperature compensating circuit is needed if variations in gas density are used to measure density as a function of altitude, since gas density also varies with temperature. The equation for gas density is:

$$P V = n R T$$

where:
  P = pressure;
  V = volume;
  n = number of molecules;
  R = gas constant; and
  T = temperature (Kelvin).

As can be seen from the equation, gas density varies linearly with temperature. Thus, a circuit which produces a linear change in the frequency of the reference oscillator in a vacuum is needed to match the change in frequency of the density oscillator resulting from air density changes due to temperature.

Thermistor 66 has a resistance which varies with temperature according to the equation:

$$R(T) = R_o(T)\, e^{\beta[(1/T) - (1/T_o)]}$$

where:
  $\beta$ = material constant of the thermistor; and
  T and T$_o$ = absolute temperatures in degrees Kelvin.

Although not linear, the voltage produced at the junction of thermistor 66 and resistor 70, where R(T) = resistance of thermistor 66 and R70 = resistance of resistor 70, varies linearly with temperature. This produces a voltage across varactor 64 which varies linearly with temperature. To give a linear change in oscillator frequency as a result of this linear change in voltage, a varactor 64 is chosen with a capacitance vs. voltage curve which matches the capacitance vs. Δf/fo characteristic of the crystal oscillator (where Δf=change in frequency and fo=resonant frequency of the reference oscillator). The capacitance vs. voltage characteristics is given by the equation:

$$\frac{\Delta f}{fo} = \frac{.001 * Co}{(Co + C_L)} - \Delta f_{5PF}$$

where:
Co=capacitance value for fo;
$C_L$=load capacitance; and
$\Delta f_{5PF}$=change in frequency at 5 picofarads (the minimum capacitance of the varactor).

The varactor capacitance is typically given by the formula:

$$Cj = \frac{2\ C_{j4}}{(V + .85)^{.44}}$$

where:
Cj=capacitance of varactor;
Cj4=capacitance at 4 volts (typically given by manufacturer); and
V=voltage.
(The 0.85 constant and the 0.44 exponent vary for different types of varactor diodes).

The outputs of both amplifiers 14 and 16 are applied to mixer 18 and the output of mixer 18 is applied to Schmitt trigger amplifier 20.

As can be seen from FIG. 5, the output of the amplifiers is a sine wave and the output of mixer 18 is a square wave proportional to the input sine wave with a pulse width proportional to the gas density experienced by crystal 12. The Schmitt trigger amplifier serves to give a cleaner square wave with fast rise and fall times. The X-axis shows a decreasing pulse width which corresponds to gas density.

As will be understood by those familiar with the art, the present invention may be embodied in other specific forms without departing from the spirit or essential characteristics thereof. For example, a circuit other than a mixer could be used to compare the two frequencies of the reference and the measurement oscillators. This could be done, for instance, by converting the frequencies to digital form and analyzing them in a microprocessor. In addition, a temperature compensating circuit could be added to amplifier 14 rather than amplifier 16. Alternately, the temperature can be measured and a microprocessor used to correct the air density reading accordingly. Therefore, the disclosure of the preferred embodiments of the invention is intended to be illustrative, but not limiting, of the scope of the invention which is se forth in the following claims.

What we claim is:

1. A gas density transducer comprising:
a reference tuning fork crystal oscillator sealed within a chamber having a fixed gas density;
a detector tuning fork crystal oscillator exposed to the density of the gas surrounding said transducer; and
means for comparing the frequency of signals from said reference and detector oscillators and producing an output signal proportional to the difference in the frequencies of said signals.

2. The transducer of claim 1 wherein said fixed gas density is highly evacuated.

3. The transducer of claim 1 wherein said means for comparing comprises a mixer producing a beat frequency proportional to the difference between the frequencies of the signals from said reference and detector oscillators.

4. The transducer of claim 3 further comprising first and second amplifiers coupled between said reference and detector oscillators, respectively, and said mixer, and a Schmitt trigger buffer coupled to an output of said mixer.

5. The transducer of claim 4 further comprising a display coupled to an output of said Schmitt trigger buffer.

6. The transducer of claim 1 further comprising means for varying the frequency of said reference oscillator responsive to changes in temperature to substantially offset changes in frequency caused by variations in gas density due to temperature changes.

7. The transducer of claim 6 wherein said means for varying comprises a capacitor coupled at a first lead to said reference oscillator, a series combination of a resistor and a varactor diode having a junction coupled to a second lead of said capacitor, and a thermistor coupled in parallel with said series combination of said varactor diode and said resistor.

8. The transducer of claim 1 further comprising a container surrounding said detector oscillator, said container having a hole coupling the interior of said container to the surrounding gas.

9. The transducer of claim 8 further comprising a diaphram covering said hole.

10. A gas density transducer comprising:
a reference tuning fork crystal oscillator sealed within a chamber in a substantial vacuum;
a detector tuning fork crystal oscillator exposed to the pressure of the gas surrounding said transducer;
a first amplifier coupled to said detector oscillator;
a second amplifier coupled to said reference oscillator, said second amplifier including means for varying the frequency of said reference oscillator responsive to changes in temperature to substantially offset changes in frequency caused by variations in gas density due to said changes in temperature; and
a mixer for producing a beat frequency proportional to the difference between the frequencies of output signals of said first and second amplifiers.

11. A gas density transducer comprising:
a reference tuning fork crystal oscillator sealed within a chamber having a fixed gas density;
a detector tuning fork crystal oscillator exposed to the density of the gas surrounding said transducer;
means for comparing the frequency of signals from said reference and detector oscillators and producing an output signal proportional to the difference in the frequencies of said signals; and
temperature compensation means for varying said output signal inversely proportional to the change in gas density with temperature.

12. The transducer of claim 11 wherein said temperature compensation means comprises a capacitor coupled at a first lead to said refernece oscillator, a series combination of a resistor and a varactor diode having a junction coupled to a second lead of said capacitor, and a thermistor coupled in parallel with said series combination of said varactor diode and said resistor.

13. A pressure transducer comprising:
   a reference tuning fork crystal oscillator sealed with a first chamber having a fixed gas density;
   a detector tuning fork crystal oscillator mounted in a second chamber filled with a gas and having an opening coupling the interior of said chamber to the exterior of said transducer;
   a flexible diaphragm covering said opening so that changes in pressure outside said transducer will move said diaphragm to change the volume of said second chamber and thus vary the gas density in said second chamber; and
   means for comparing the frequency of signals from said reference and detector oscillators and producing an output signal proportional to the difference in the frequencies of said signals.

14. The transducer of claim 13 wherein said fixed gas density is highly evacuated.

15. The transducer of claim 13 wherein said means for comparing comprises a mixer producing a beat frequency proportional to the difference between the frequencies of the signals from said reference and detector oscillators.

16. The transducer of claim 13 further comprising temperature compensation means for varying said output signal inversely proportional to the change in gas density with temperature.

* * * * *